United States Patent [19]
Cobb

[11] Patent Number: 5,604,299
[45] Date of Patent: Feb. 18, 1997

[54] METHOD OF LOCATING EMISSION SOURCES

[75] Inventor: Ronald F. Cobb, Humble, Tex.

[73] Assignee: Sensible Technologies, Inc., Houston, Tex.

[21] Appl. No.: 451,141

[22] Filed: May 26, 1995

[51] Int. Cl.$^6$ .................................................. G01M 3/04
[52] U.S. Cl. ................................. 73/31.02; 73/40
[58] Field of Search ...................... 73/23.2, 31.01, 73/31.02, 31.03, 40

[56] References Cited

U.S. PATENT DOCUMENTS

| | | | |
|---|---|---|---|
| 3,780,566 | 12/1973 | Smith et al. | 73/23.2 X |
| 4,135,092 | 1/1979 | Milly | 73/31.02 X |
| 4,204,121 | 5/1980 | Milly | 73/31.02 X |
| 5,297,421 | 3/1994 | Hosonuma et al. | 73/40 |
| 5,406,265 | 4/1995 | Trozzo et al. | 73/31.02 X |

FOREIGN PATENT DOCUMENTS

| | | | |
|---|---|---|---|
| 1-219533 | 9/1989 | Japan | 73/31.02 |

*Primary Examiner*—Michael Brock
*Attorney, Agent, or Firm*—Arthur M. Dula

[57] ABSTRACT

A method of locating the source of material emitted into a moving fluid by measuring the mass flux of the emitted material in each direction of fluid flux over a period of time at a plurality of sensing points; smoothing these directional mass flux values by including a component of mass flux values taken from the adjacent fluid direction and then preparing a map of potential emission values of the emitted material at each point in a plane reasonably adjacent to the sensing points.

7 Claims, 5 Drawing Sheets

(2 of 5 Drawing(s) in Color)

METHOD OF LOCATING EMISSION SOURCES

BACKGROUND OF THE INVENTION

1. Technical Field of the Invention

The present invention relates generally to methods of locating the position of sources emitting material into a fluid. More specifically, the present invention relates to methods of locating sources of airborne pollution over an area. The area is reasonably approximate to the invention.

2. Description of the Related Art

In order to legally and technically control pollution, it is necessary to locate, with reasonable accuracy, the point or points from which a pollutant is released into the biosphere. Only then can responsibility be assigned and remedial measures taken. In an industrial context, location is a difficult task because many potential sources of pollution are located together in industrial parks and the wind carries the pollutants from their source or sources in a variable manner.

In the past, many techniques have been developed to sense or locate emission sources. In broad outline, these prior methods fall into two categories: remote sensing and sample collection.

Remote sensing, whether ground-, air- or space-based, relies on detection of a physical characteristic of the pollutant, usually its electromagnetic (i.e., U.V., visible or I.R.) spectra. This spectra is monitored by either passively observing the spectra, as by airborne or satellite imaging, or by passing a laser beam through the atmosphere and observing the resultant spectra. While this method works well for some types of pollutants, it is generally not sensitive and, thus, requires a large presence of pollutants in the atmosphere to be useful. Many types of pollution do not have an optical spectra that is easily measured. Many pollutants are dangerous and illegal at concentration levels too low to be detected using current remote sensing technology. Normally, remote sensing by an optical signal establishes a measurement along a line. However, that measurement cannot typically locate the source of an airborne emission, when there is wind, if the remote sensing instrumentation is stationary, and only pointed in one direction.

Sample collection is used widely for the detection of pollutants of all kinds. The prior art teaches many systems for taking and analyzing atmospheric samples. Usually the pollutants in such samples are identified and their concentration is measured by an analytic means, e.g., a gas/liquid chromatograph. This instrument operates by passing a sample through a chromatographic column packed with an inert support upon which a nonvolatile coating has been deposited. As the sample passes through the column, individual molecules are absorbed and then released at different times from the column's surface. If a column of the proper type is employed, the components of the sample emerge from the column completely separated from each other, with the most strongly absorbed component emerging last. This emerging stream then passes through a detector, which detects each component by means of thermal conductivity, reaction to ionization, or other well known technique. The advantage of the gas/liquid chromatograph over the optical spectrometer is that it can make nearly simultaneous measurements of many components and can detect very low concentrations of pollutants in the one part per billion or trillion range. Although the chromatograph can determine what pollutants are present in a sample, it cannot provide information about the location of the source of the pollution unless many samples are analyzed from points close to the source.

The prior art teaches the use of mobile sampling stations which are usually mounted in a vehicle which traverses areas suspected of being the source of pollutants. This works well where the mobile sampler can go into the area, but it is not well suited for continuous monitoring of a site, both because of the great expense of such mobile systems and the fact that they must operate close to the emission source to make an accurate map of its location. In many cases, such as in an industrial park, refinery, chemical plant or waste dump, it is practically impossible to use a mobile sampling system because there are not enough roads inside or around the facility. In many cases, it is desirable to maintain a continuous pollution monitoring system around the industrial facility. At present, the prior art teaches systems such as stainless steel sample cans that are opened to obtain and hold atmosphere samples on a controlled basis. Such systems can only report the average concentration of a pollutant over a long period of time. They are very expensive. It is necessary to take many samples within the suspect area to reliably locate the source of emission of the pollutant.

In summary, then, the prior art teaches the location of some sources of emission of pollution by remote sensing, but this method is not effective at low levels of emission and doesn't work for all pollutants. Sample collection and analysis by gas/liquid chromatography provides high sensitivity and can measure many pollutants, but does not locate the source of emission unless many samples are taken close to the emission source.

SUMMARY OF THE INVENTION

The present invention is a method of locating emission sources with reasonable accuracy by measuring the concentration, calculating the directional mass flux of the emitted material at a plurality of sensed points, and then preparing a map of potential emission values for the emitted material for the area surrounding the sensed points.

A primary benefit of the present invention is that it provides a method of calculating a map of potential emission sources that combines the large and small area mapping result obtained by optical remote sensing with the high sensitivity and broad range of simultaneous measurements made possible by chromatographic analysis or by any device with acceptable sensitivity to detecting chemicals.

Another benefit of the present invention is to provide a method that can be used for continuous monitoring of specific emission sites over large or small areas.

Yet a further benefit of the present invention is that it can locate unknown emission sources over a large or small area using data gathered outside the area of interest.

BRIEF DESCRIPTION OF THE DRAWINGS

The file of this patent contains at least one drawing executed in color. Copies of this patent with color drawing(s) will be provided by the Patent and Trademark Office upon request and payment of necessary fee.

BEST MODE FOR CARRYING OUT THE INVENTION

The first step in practicing the method taught by the present invention is to obtain a set of field data. This data comprises reasonably synchronous measurements of wind direction, wind speed and the concentration of the sensed material over a period of time for each of several points. The concentration, wind direction and wind speed must be measured reasonably simultaneously. It is important to the proper use of the present invention that wind speed, wind direction and concentration be correlated so that the mass flux of the emitted material, which will hereinafter be called a pollutant, can be averaged for all readings where the wind is from a given direction.

Measurement of wind speed may be made in a conventional manner as has been well-known in the art through the use of an anemometer. The measurement of wind direction may be measured by means of a directional wind vane. Concentration information may be obtained by any convenient analytic method. Gas/liquid chromatography may be used because of its great sensitivity to many types of potential pollutants, its ability to simultaneously measure multiple pollutants and its low cost. However, any reasonably continuous method of sensing of the pollutant may be used as, for example, the use of a spectraphotometer. The measurement of these variables is well-known to those skilled in the art of pollution detection and atmospheric monitoring. The sensed measurements of concentration, wind direction, wind speed and time may be recorded by a data logging system, which may be of any convenient type, preferably a general purpose computer operating under the control of an algorithm adapted to record the information on magnetic tape or disc.

It is critical to the present invention that the measurements of time, concentration, wind direction and wind speed at each individual sensing point be made reasonably simultaneously. This raw information may be gathered for any convenient period of time; a day, a week, a month, a year. It may be gathered by one station that is moved from point to point around the area of interest, or it may be measured by a plurality of stations. It is not important that the measurements of the plurality of stations be synchronized with each other. It is necessary that the measurement of the wind speed, wind direction and concentration at each station be synchronized.

The raw data from the simultaneous field measurements of concentration, wind speed and wind direction is stored as a database, the "station contribution array". The information contained in this database is the location of the measuring station, the concentration, the wind speed and the wind direction for each measurement.

Figure 1:
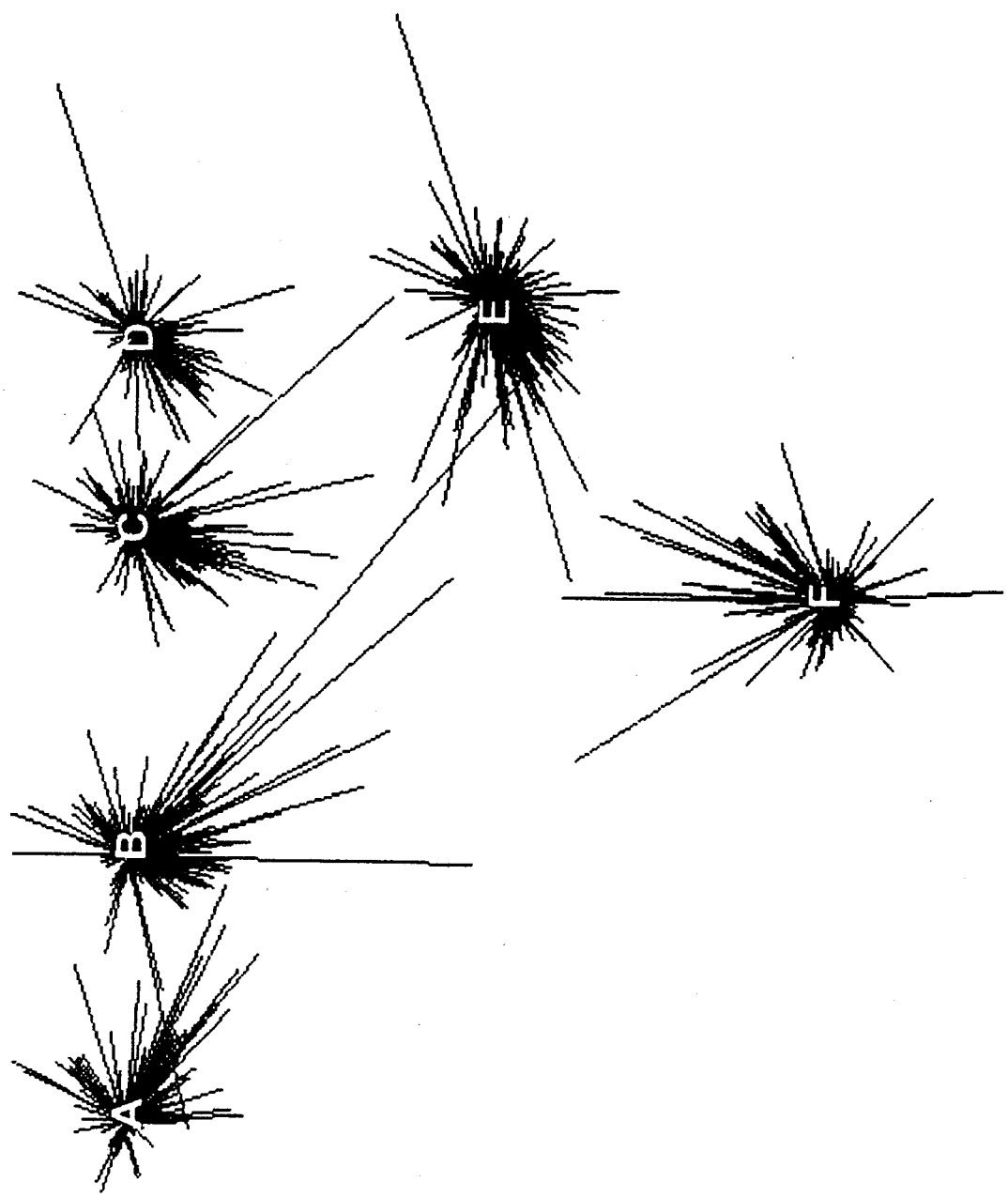
FIG. 1 is a diagram showing the station contribution array for a six station data set according to the preferred embodiment of the present invention.

As an example of one way to practice the method of the preferred embodiment of the present invention, the station contribution array is constructed for six (6) different geographical locations as shown in FIG. 1. Each measurement made at one of these locations includes wind speed, wind direction, station i.d., and concentration.

This data is then sorted by wind direction, which for the purpose of this illustration is divided into the 360 degrees of the compass. The wind direction need not necessarily be measured degree by degree. Wind direction may be measured at any desired resolution, though higher resolutions yield better results.

It is important to emphasize that the concentration measurements at each station need not be made during the same time period. It is possible for a single measuring device to be moved from location to location to collect the data, if it can be safely assumed that the source of the pollution is continuous during the period of all the measurements.

Once the raw data is sorted, the resulting data set will comprise a plurality of correlated wind speed and concentration readings for each direction of the wind. This raw information is combined into averages for each angle for each of the six locations. Wind direction is measured to the closest degree and all readings of concentration multiplied by the wind speed (which is mass flux) are averaged for each of these 360 directions. Then a mass flux rose can be generated for each sensing station as is shown in FIG. 1.

FIG. 1 is a visual representation of the data arrays for average mass flux around 360 degrees for the six (6) measuring stations, A through F. Shown are 360 lines, or rays, emanating from each monitoring station. The length of each ray is proportional to the average incoming mass flux to the measuring station. Each of the rays is pointing in the direction from which the measurement was taken, i.e., into the mass flux. The origin of the arrays is placed on the diagram in the same relationship as their physical locations at the sensed site.

In order to obtain a numerical value that is proportional to the mass flux (as measured in pounds per hour, grams per second, etc., on a per unit area basis), each of the measured concentrations is multiplied by the wind speed for each reading that is associated with the detectable wind speed. Concentration measurements made while the wind speeds are below the detection limits of the wind speed measuring device are discarded. Additionally, it may be desirable to filter from the data those readings associated with certain conditions, such as wind speed, wind direction or concentration. One reason for this, for the example of wind speed, is that as the wind speed increases, the signal becomes more directional because the pollutant plume is thinner.

Once this station contribution array is complete, the "mapping array" can be calculated.

Figure 2:
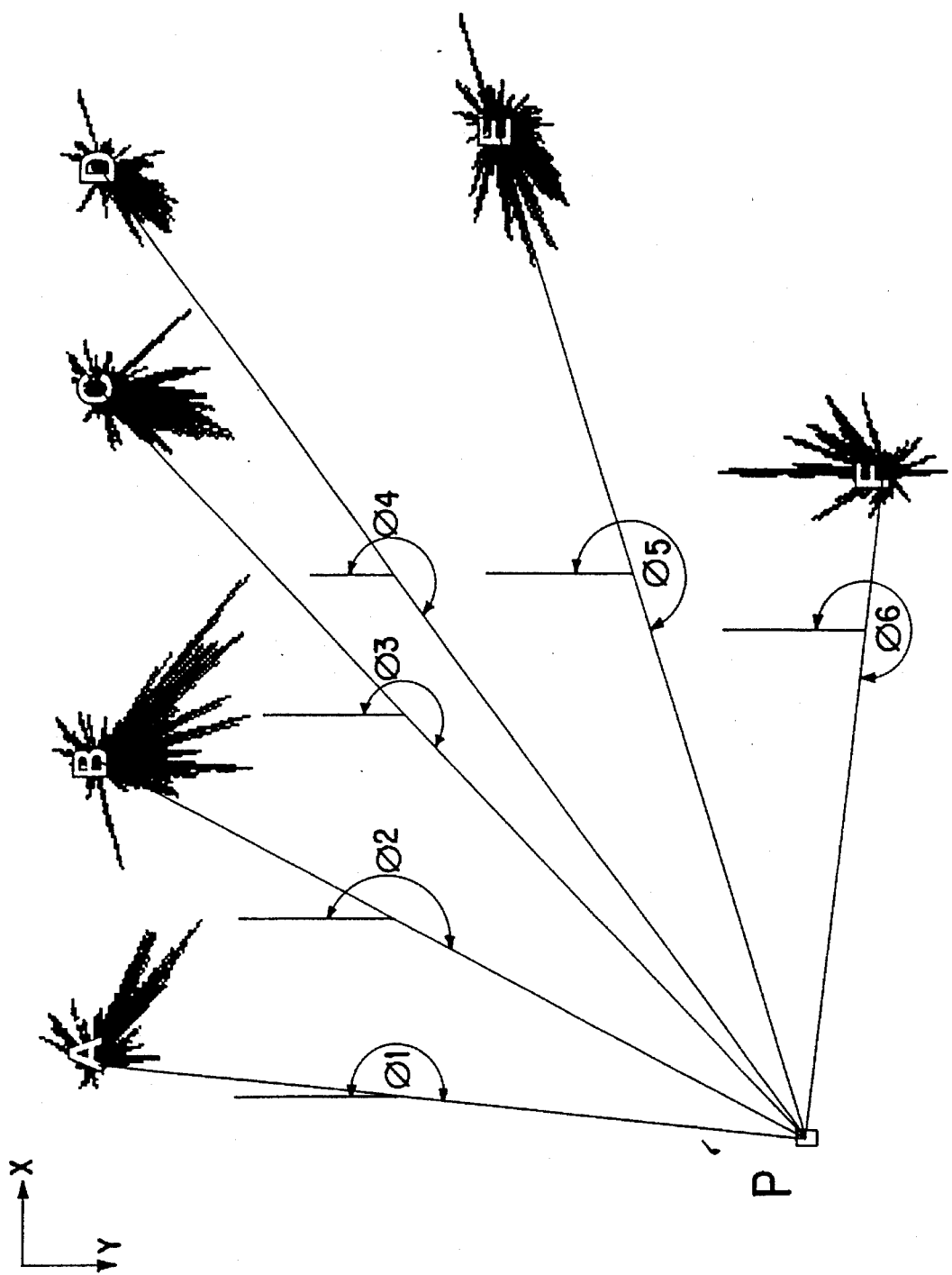
FIG. 2 is a diagram showing the method of mapping the concentration or mass flux at a point from the data of FIG. 1.

As is shown in FIG. 2, an area of interest is selected. In FIG. 2, this area of interest is indicated by the double lines at the exterior of the drawing. This area is in reasonable proximity to the measuring stations. The selection of an area of interest is not dependent upon the exact placement of the sensing stations. Therefore, it is possible to consider many different areas of interest, and to generate their associated mapping arrays, for each station contribution array.

The geographic area of interest is divided into a grid of Cartesian points (x, y). Increasing the number of points within the area of interest increases the resolution or fineness of the resulting map. It should be noted that the monitoring stations need not be inside the area of interest. In fact, they can be located anywhere reasonably proximate to the area of interest.

As show in FIG. 2, for each grid point $P_{xy}$ in the area of interest, the compass angle theta 1 through theta 6 is calculated for each of the measuring stations A through F, respectively. These angles, when rounded to the unit resolution of the wind direction, in the present example one degree, selects the rays from each of the stations that makes up a contribution to the mapping array at point P. The data from all of the measuring stations that points along the ray to point P are summed and then the average value is calculated. The resulting number represents the potential of this individual point as being the single source of the measured pollutant. This value can be the average mass flux or the average concentration at point P. In practice, the average mass flux has proven to be more effective than the use of concentration for the detection of emissions sources.

Figure 3:
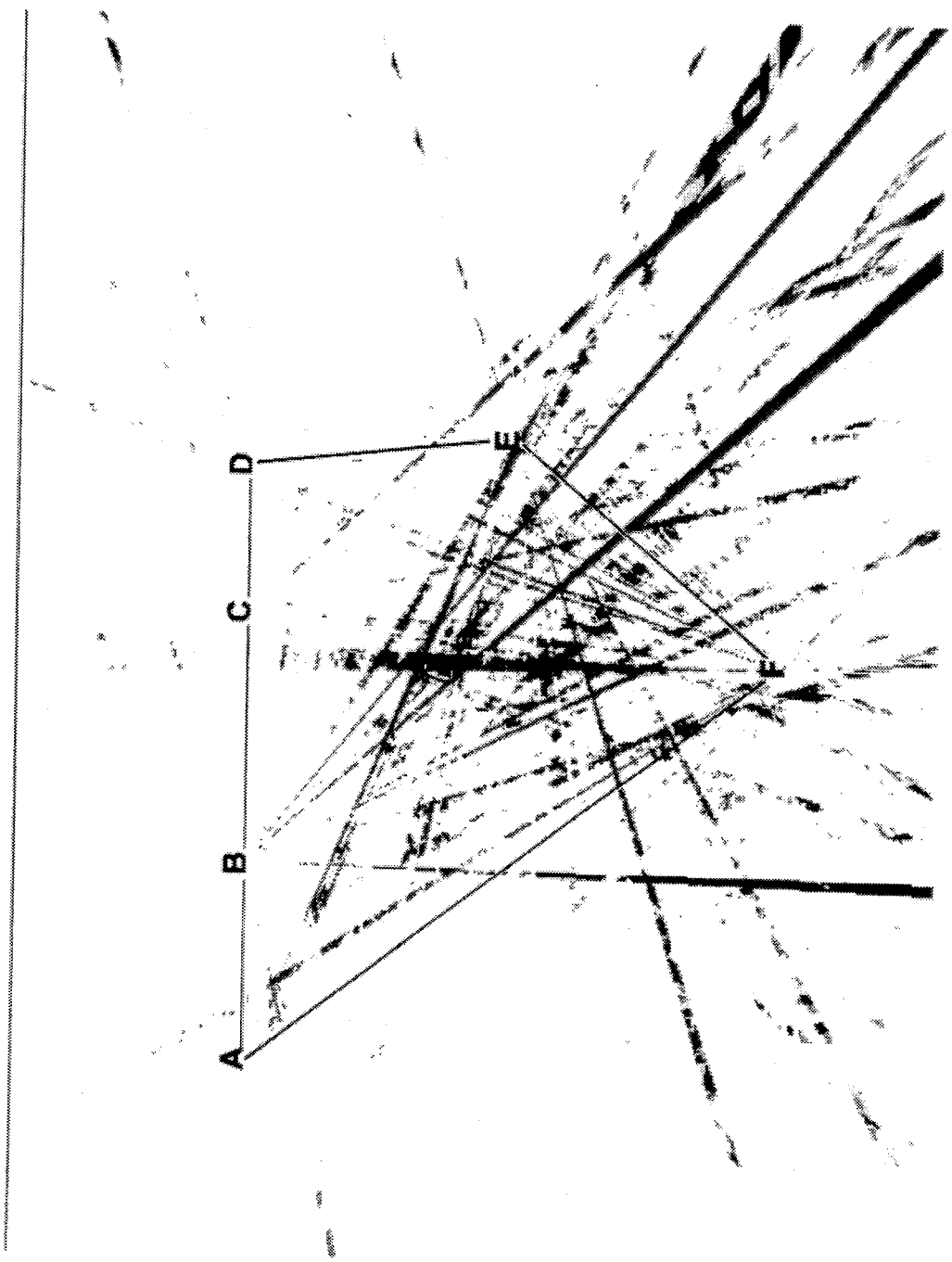
FIG. 3 shows a mapping array created from the data set of FIG. 1.

This mapping process is then repeated for each discrete point within the area of interest. The resulting map of potential values is a "mapping array". This map displays the potential for each of the points within the area of interest to be the single source of the measured pollutant. This mapping array is shown in FIG. 3. In FIG. 3, colors are assigned to ranges of potentials displayed at each point in the area of interest. In FIG. 3, white is assigned the lowest range of potential beginning with zero. Yellow, blue and red are used, in sequence, to describe the subsequently higher ranges of potential.

The data presented in this form results in numerous rays of color and polygon shapes, as is clearly shown in FIG. 3. The station letters and the lines connecting the monitoring stations were added to clarify the image.

Although the mapping array, as shown in FIG. 3, has some utility, it may be desirable, though it is not required, to smooth the data to make the mapping array easier to interpret. This can be done by applying a smoothing function to the numeric values in the station contribution array or to the mapping array, or to both. In practice, the inventors have found that the smoothing of the station contribution array is most effective. The smoothing technique creates a new value for the mass flux in each direction (and for concentration, if the value of concentration is used in the mapping program) for each angle in the array.

A smoothing algorithm that has proven effective uses the following equation:

$$Pn_{(x)} = a \cdot Po_{(x-1)} + b \cdot Po_{(x)} + c \cdot Po_{(x+1)}$$

Suggested values: a=0.25, b=0.50, and c=0.25
Pn=new value for potential
Po=previous value for potential
x=wind direction angle (1–360) i.e. 43 is wind direction angle 43
For each possible measured angle: x=1 through 360 degrees This smoothing algorithm may be repeated numerous times. The effect is to include in the calculation of the mass flux vector a contribution from each of the adjacent mass flux vectors. The smoothing initially enhances the image presented by the mapping array, but then the image slowly degrades as all the directional mass flux values approach the station average.

Figure 4:
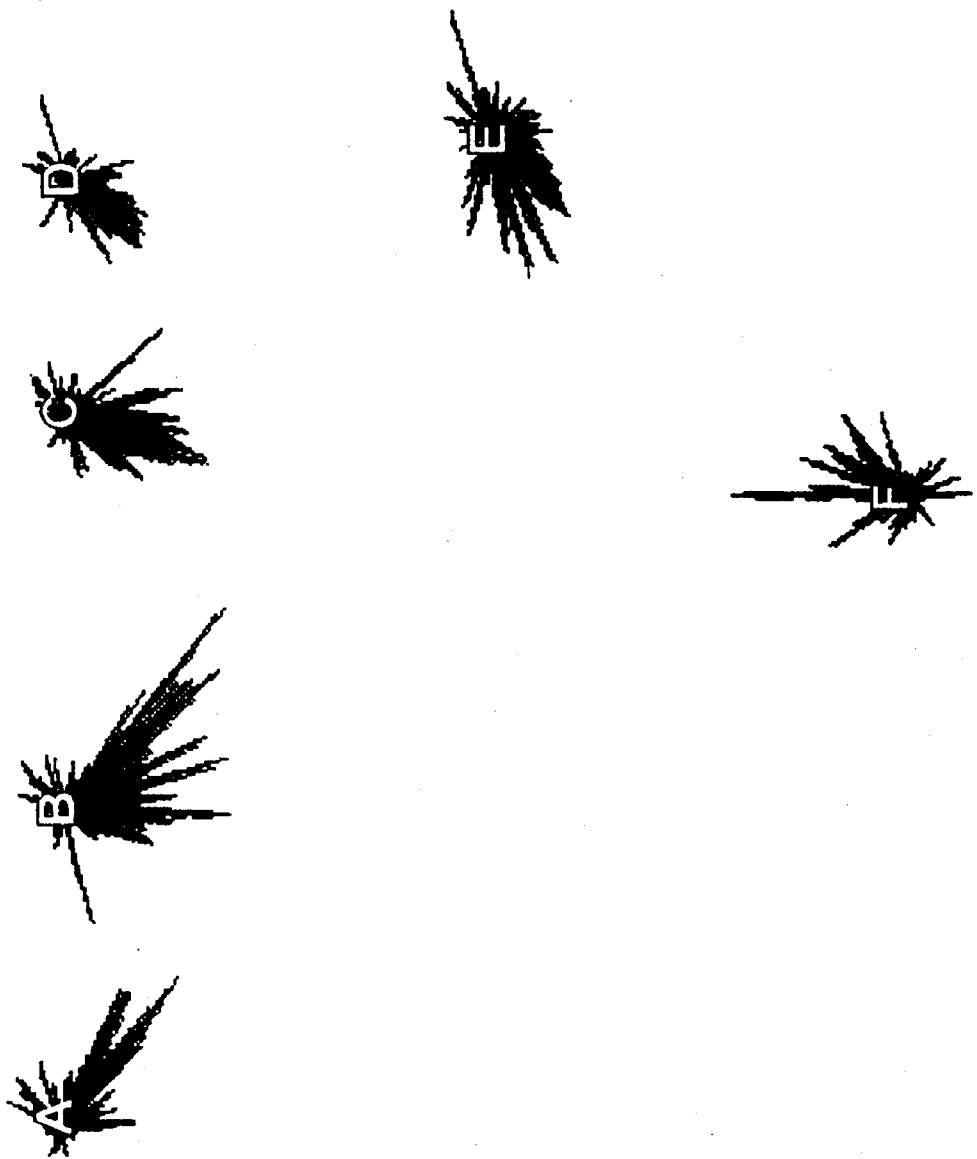
FIG. 4 shows the station contribution array of FIG. 1 after smoothing.

In FIG. 4, four passes of the smoothing algorithm set forth above were applied to the station contribution array of FIG. 1.

Figure 5:
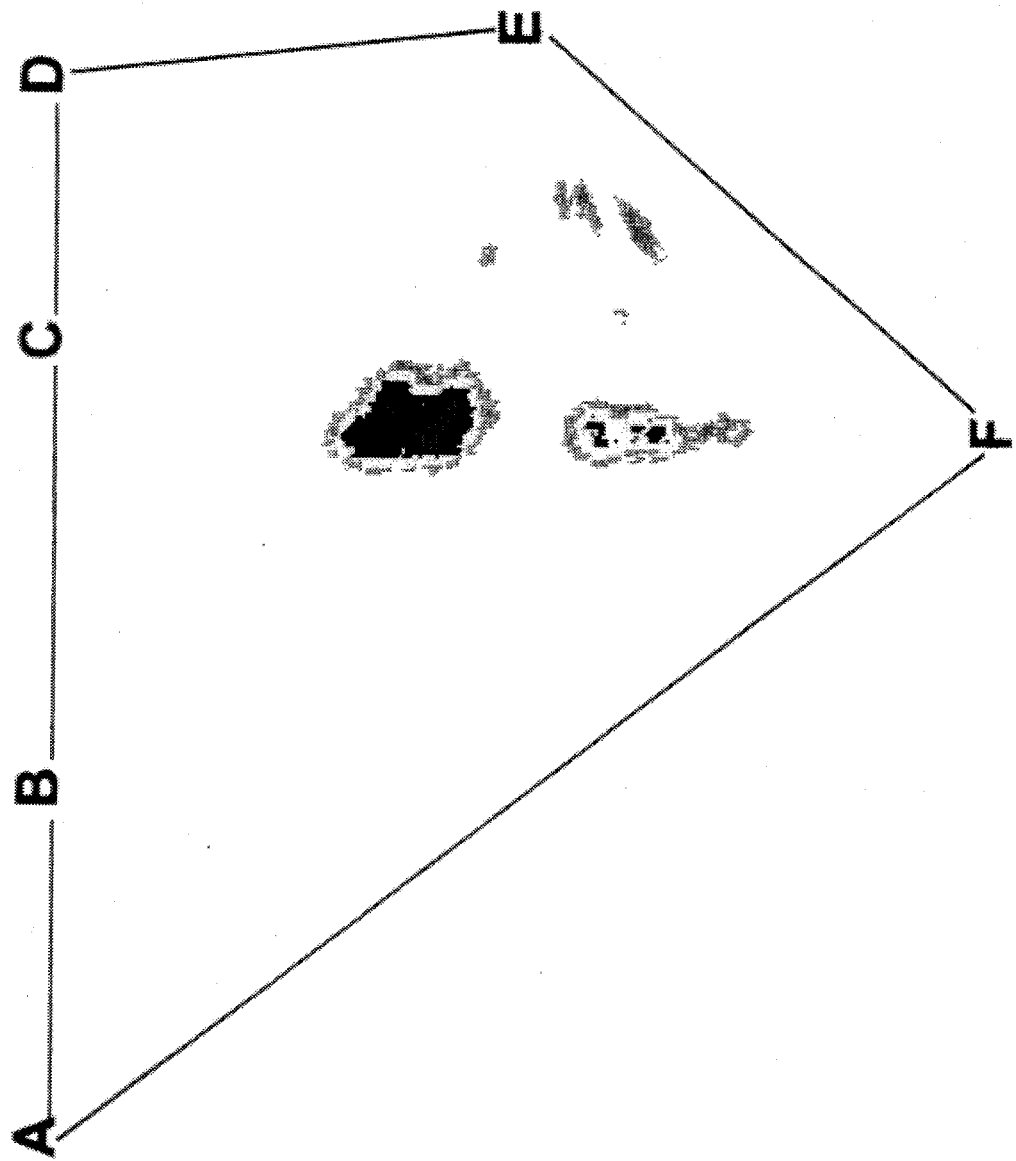
FIG. 5 shows the mapping array with smoothing calculated from the station contribution array of FIG. 4.

The method of calculating the theoretical potential mass flux or concentration field described in connection with FIG. 3, above, is used with the smoothed station contribution arrays of FIG. 4 to produce the smoothed mapping array shown in FIG. 5. This significantly refines the location of the source of the emission. The red area shown in FIG. 5 shows the most likely source of emission.

From their experimental work with this invention, the inventors have determined that exclusion of an entire measuring station's data located close to a source will sometimes improve the resolution of the location of secondary sources. It is also sometimes useful to restrict raw data to certain time intervals to evaluate the events within that period. As was mentioned above, it is useful to reject wind speed below a certain value and to exclude these measurements from the preparation of the station contribution array. This is because the dispersal angle of a chemical plume decreases with an increasing wind speed; thus, concentration information from a given direction at a higher wind speed has a higher angular accuracy.

As a practical matter, when working with computer display systems to present the data from this method, it is often convenient to match the x and y range of the values for the area of interest, as was shown above in connection with FIG. 2, to the pixel height and width ratios of the computer display being used.

The present invention, therefore, provides a useful technique for locating an emission source through calculation of mass flux based on measurements of wind direction, wind speed, and component concentration in an area reasonably adjacent to the sensed positions. Smoothing assists the visual presentation of the data. Many different smoothing algorithms may be used to practice the present invention.

The inventors have disclosed the best method known to them as of the date of the application of practicing the present invention. However, many different methods of manipulating, storing and presenting data may be used by the present invention. Thus, the present invention should be limited only by the appended claims and their equivalents.

Appendix

```
'Emission Source Locator Software
'Copyright (C) 1995 Sensible Technologies, Inc.
'You can convert an angle measurement from degrees to radians by
'multiplying the degrees by ã/180, where ã = 3.141593.

'DEFINT R
DECLARE SUB CIT (XC(), YC(), Srose1(), SROSE2(), SROSE3(), SROSE4(), SROSE5(), SROSE6(), SROSE7(), c1, c2, c3, c4, c5)
DECLARE SUB IRANDOM (RON())
DECLARE SUB SHOW (Srose1(), X1, x2, K, SCALE, kolor)
DECLARE SUB SMOOTH (XRoseZ(), SROSEZ())
DECLARE SUB ARCTAN (X1%, Y1%, DEG%)
DECLARE SUB SCRDP (XC(), YC(), c1, c2, c3, c4, c5)
DECLARE SUB RAWIN (ROSE1(), rose2(), ROSE3(), ROSE4(), ROSE5(), ROSE6(), ROSE7())
'DECLARE SUB indata (A!)
'DECLARE SUB massRose (K!, SCALE!, kolor!)
DECLARE SUB SHOWWIND (ROSE1(), xa, yb, K, SCALE, kolor)
CLEAR , , 40000

NELE% = 360
FIVE% = 5
SIXTY% = 60

DIM SHARED ROSE1(NELE%, FIVE%)
DIM SHARED XRose1(NELE%)
DIM SHARED Srose1(NELE%)
DIM SHARED rose2(NELE%, FIVE%)
DIM SHARED xROSE2(NELE%)
DIM SHARED SROSE2(NELE%)
DIM SHARED ROSE3(NELE%, FIVE%)
DIM SHARED xROSE3(NELE%)
DIM SHARED SROSE3(NELE%)
DIM SHARED ROSE4(NELE%, FIVE%)
DIM SHARED xROSE4(NELE%)
DIM SHARED SROSE4(NELE%)
DIM SHARED ROSE5(NELE%, FIVE%)
DIM SHARED xROSE5(NELE%)
DIM SHARED SROSE5(NELE%)
DIM SHARED ROSE6(NELE%, FIVE%)
DIM SHARED xROSE6(NELE%)
DIM SHARED SROSE6(NELE%)
DIM SHARED ROSE7(NELE%, FIVE%)
DIM SHARED xROSE7(NELE%)
DIM SHARED SROSE7(NELE%)
DIM SHARED TABLE(SIXTY%)

'Element 1 is total velocity #
'Element 2 is number of samples in velocity number
'Element 3 is total concentration #
'Element 4 is number of samples in concentration
'Element 5 is Total mass flow #
'Element 6 is average mass flow
'Element 7 is smoothed mass flow 'Main element corresponds in element number to direction
DIM XC(7), YC(7), xs(7), ys(7)
DIM lc$(7), lcx$(7), SCALE, FFFF$ '***********LOAD DATA TABLE
'SET UP TABLE OF ARCTAN VALUES FOR USE BY ARCTAN SUBROUTINE
'========================================================
'CODE BETWEEN ========== MUST BE IN THE MAIN PROGRAM pi = 3.1416
```

15

Copyright © 1995 Sensible Technologies, Inc.　　　　Emission Source Locator Software

CLS

*16*

Copyright © 1995 Sensible Technologies, Inc.

Emission Source Locator Software

```
'CALCULATE TABLE VALUES
FOR I = 0 TO 58
TABLE(I) = FIX((ATN(I / 58) * 180 / pi) + .5)
'  PRINT USING "###   ###.#### "; i; TABLE(i)
NEXT I

'ron is used as temporary storage array

SCREEN 12
K = 7 ' element to plot
kolor = 15'Bright White
        c1 = 82 'defalt color cuts
        c2 = 75
        c3 = 50
        c4 = 25

SCALE = 6'*********scaling factor
'********Defalt location of AQMS stations
YC(1) = 120
    XC(1) = 100
YC(2) = 120
    XC(2) = 204
YC(3) = 120
    XC(3) = 332
YC(4) = 120
    XC(4) = 409
YC(5) = 271
    XC(5) = 166
YC(6) = 260
    XC(6) = 424
YC(7) = 399
    XC(7) = 307
FOR I = 1 TO 7
    xs(I) = XC(I)
    ys(I) = YC(I)
NEXT I
convert = (3.141593 / 180) 'Constatnt
SMTH$ = "." ' LEVEL OF SMOOTHING 0=NONE
ZIN$ = ""
DO WHILE NOT ZIN$ = "Q"
LOCATE 2, 1 'CLEAR LINE 2
PRINT "                                        "
LOCATE 2, 1 'PRINT MENU ON LINE 2
PRINT "1= Change settings  2= I/O  3= Display  4= Clear Screen"
LOCATE 1, 8
PRINT "           "; FFFF$; " "; c1; c2; c3; c4; SM
LOCATE 1, 1 ' PROMPT FOR MAIN OPTIONS
INPUT "Option?", ZIN$ IF ZIN$ = "1" THEN '************CHANGE SETTINGS*************
    LOCATE 2, 1
    PRINT "                                        "
    LOCATE 2, 1
    PRINT "1= SMOOTING  2= ROSE SCALE 3= SCREEN COLOR CUTS 4= SCALE SITE"
    ZIN1$ = ""
    LOCATE 1, 8
    PRINT "  "
    LOCATE 1, 1
    INPUT "Option?", ZIN1$
```

```
IF ZIN1$ = "1" THEN '****SMOOTHING
'INSERT 1
'INSERT 1

' LOCATE 1, 1
' ZIN4$ = ""
' INPUT "Option?", ZIN4$
LOCATE 2, 1' CLEAR INSTRUCTION LINE
PRINT "                                       "
LOCATE 2, 1
PRINT "0= NO SMOOTHING  #=LEVEL OF SMOOTING"
SMTH$ = "."
LOCATE 1, 8
PRINT "   "
LOCATE 1, 1
INPUT "Option?", SMTH$
SM = VAL(SMTH$)
 IF SM = 0 THEN
     FOR J = 1 TO 360

Srose1(J) = XRose1(J)
          SROSE2(J) = xROSE2(J)
          SROSE3(J) = xROSE3(J)
          SROSE4(J) = xROSE4(J)
          SROSE5(J) = xROSE5(J)
          SROSE6(J) = xROSE6(J)
          SROSE7(J) = xROSE7(J)
     NEXT J
 END IF
 IF SM > 0 THEN
     FOR I = 1 TO SM
          CALL SMOOTH(Srose1(), Srose1())
          CALL SMOOTH(SROSE2(), SROSE2())
          CALL SMOOTH(SROSE3(), SROSE3())
          CALL SMOOTH(SROSE4(), SROSE4())
          CALL SMOOTH(SROSE5(), SROSE5())
          CALL SMOOTH(SROSE6(), SROSE6())
          CALL SMOOTH(SROSE7(), SROSE7())

NEXT I
  END IF

END IF

IF ZIN1$ = "2" THEN '****SCALE ROSE

' LOCATE 1, 1
' ZIN5$ = ""
' INPUT "Option?", ZIN5$
LOCATE 2, 1' CLEAR INSTRUCTION LINE
PRINT "                                       "
LOCATE 2, 1
PRINT "INPUT SCALE FACTOR 1.0 = NO CHANGE"
LOCATE 1, 8
PRINT "   "
LOCATE 1, 1
HX = 1!
INPUT "Option?", HX
IF HX > 0 THEN
 SCALE = SCALE * HX
 END IF
END IF
```

```
IF ZIN1$ = "3" THEN '*** COLOR CUTS
    LOCATE 2, 1' CLEAR INSTRUCTION LINE
    PRINT "                                              "
    LOCATE 2, 1
    PRINT "c1+=red c2+=blue c3+=yellow c4+=gray >c4=white"
    SMTH$ = "."

LOCATE 2, 50
    INPUT "New C's", c1, c2, c3, c4

END IF

IF ZIN1$ = "5" THEN '*** SCALE SITE
        CALL CIT(xs(), ys(), Srose1(), SROSE2(), SROSE3(), SROSE4(), SROSE5(), SROSE6(), SROSE7(), c1,
c2, c3, c4, c5)

END IF

IF ZIN1$ = "4" THEN '*** SCALE SITE
    LOCATE 1, 1
    PRINT "           "
    LOCATE 2, 1' CLEAR INSTRUCTION LINE
    PRINT "                                              "
    LOCATE 2, 1
    PRINT "PO1 X="; xs(1); " Y="; ys(1);
    LOCATE 2, 25
    INPUT "INPUT NEW X,Y", XN!, YN!
    PRINT "                                  "
    LOCATE 2, 1
    INPUT "INPUT SCALLING FACTOR", SIZING!

A = XN!
    B = xs(1)

DXP = A - B
    A = YN!
    B = ys(1)

DYP = A - B
    FOR I = 1 TO 7
    xs(I) = XC(I) + DXP
    ys(I) = YC(I) + DYP
        BIC = (xs(I) - xs(1)) * SIZING
        'BIC = BIC * SIZING
    xs(I) = xs(1) + BIC
    'PRINT SIZING!; XS(1), XS(I); XC(I)
        BIC = (ys(I) - ys(1)) * SIZING
        'BIC = BIC * SIZING
    ys(I) = ys(1) + BIC
    'PRINT SIZING!; XS(1), XS(I); XC(I); BIC
    NEXT I

END IF
END IF
```

```
IF ZIN$ = "2" THEN '*************I/O****************
    LOCATE 2, 1
    PRINT "                                                                    "
    LOCATE 2, 1
    PRINT "1= Process Raw Data File  2= Save Processed Data 3= Get Process Data"
    ZIN2$ = ""
    LOCATE 1, 8
    PRINT "  "
    LOCATE 1, 1
    INPUT "Option?", ZIN2$ IF ZIN2$ = "1" THEN '***PROCESS RAW DATA
' OPEN file [FOR mode] [ACCESS access] [lock} AS [#]filenum [LEN=reclen]
            LOCATE 2, 1
            PRINT "                                                            "
            LOCATE 2, 1
            INPUT "Raw Data File Name =", B$
            FFFF$ = B$
            OPEN B$ FOR INPUT AS #1
            LOCATE 3, 1
            FOR I = 1 TO 13
            INPUT #1, A$
            PRINT A$;
             NEXT I
            PRINT ""

'Element 1 is total velocity #
            'Element 2 is number of samples in velocity number
            'Element 3 is total concentration #
            'Element 4 is number of samples in concentration
            'Element 5 is Total mass flow #
            'xrose is average mass flow
            'srose is smoothed mass flow
                '***************get raw data for non calm data***************
            'Rose 2 elements 1 and 2 contain calm concentrations and frequency

Q = 0
            DO WHILE NOT EOF(1)

INPUT #1, Idate$, Itime$, IWspeed$, IWspeedx$, Idir$, Idirx$, Isec$, Isecx$, Id$, Ic$(1), Icx$(1), Ic$(2),
Icx$(2), Ic$(3), Icx$(3), Ic$(4), Icx$(4), Ic$(5), Icx$(5), Ic$(6), Icx$(6), Ic$(7), IcxS(7)
               IWspeed = VAL(IWspeedS)

IF IWspeedx$ = "v" AND IWspeed < 1.01 THEN 'capture calm cond
                 FOR I = 1 TO 7
                 IF Icx$(I) = "v" THEN
                   rose2(I, 1) = VAL(IcS(I)) + rose2(I, 1)
                   rose2(I, 2) = rose2(I, 2) + 1
                 END IF
                 NEXT I
                 END IF IF IWspeedx$ = "v" AND IWspeed > 1 THEN  'valid wind speed
                   Q = Q + 1
                   D = VAL(Idir$)'direction in degrees

D = D + 44
```

```
'***********adjust angle
       IF D > 360 THEN D = D - 360

ROSE1(D, 1) = ROSE1(D, 1) + IWspeed
    ROSE1(D, 2) = ROSE1(D, 2) + 1
  IF IcxS(1) = "v" THEN
    conc = VAL(Ic$(1))
    ROSE1(D, 3) = ROSE1(D, 3) + conc'set concentration into array
    ROSE1(D, 4) = ROSE1(D, 4) + 1
    ROSE1(D, 5) = ROSE1(D, 5) + IWspeed * conc
    IF ROSE1(D, 5) > 32000 THEN PRINT "tilt1"

END IF
  IF Icx$(2) = "v" THEN
    conc = VAL(Ic$(2))
    rose2(D, 3) = rose2(D, 3) + conc'set concentration into array
    rose2(D, 4) = rose2(D, 4) + 1
    rose2(D, 5) = rose2(D, 5) + IWspeed * conc
    IF rose2(D, 5) > 32000 THEN PRINT "tilt2"
  END IF
  IF Icx$(3) = "v" THEN
    conc = VAL(Ic$(3))
    ROSE3(D, 3) = ROSE3(D, 3) + conc'set concentration into array
    ROSE3(D, 4) = ROSE3(D, 4) + 1
    ROSE3(D, 5) = ROSE3(D, 5) + IWspeed * conc
    IF ROSE3(D, 5) > 32000 THEN PRINT "tilt3"
  END IF
  IF Icx$(4) = "v" THEN
    conc = VAL(Ic$(4))
    ROSE4(D, 3) = ROSE4(D, 3) + conc'set concentration into array
    ROSE4(D, 4) = ROSE4(D, 4) + 1
    ROSE4(D, 5) = ROSE4(D, 5) + IWspeed * conc
    IF ROSE4(D, 5) > 32000 THEN PRINT "tilt4"
  END IF
  IF IcxS(5) = "v" THEN
    conc = VAL(Ic$(5))
    ROSE5(D, 3) = ROSE5(D, 3) + conc'set concentration into array
    ROSE5(D, 4) = ROSE5(D, 4) + 1
    ROSE5(D, 5) = ROSE5(D, 5) + IWspeed * conc
    IF ROSE5(D, 5) > 32000 THEN PRINT "tilt5"
  END IF
  IF Icx$(6) = "v" THEN
    conc = VAL(Ic$(6))
    ROSE6(D, 3) = ROSE6(D, 3) + conc'set concentration into array
    ROSE6(D, 4) = ROSE6(D, 4) + 1
    ROSE6(D, 5) = ROSE6(D, 5) + IWspeed * conc
    IF ROSE6(D, 5) > 32000 THEN PRINT "tilt6"
  END IF
  IF Icx$(7) = "v" THEN
    conc = VAL(Ic$(7))
    ROSE7(D, 3) = ROSE7(D, 3) + conc'set concentration into array
    ROSE7(D, 4) = ROSE7(D, 4) + 1
    ROSE7(D, 5) = ROSE7(D, 5) + IWspeed * conc
    IF ROSE7(D, 5) > 32000 THEN PRINT "tilt7"
  END IF
END IF LOCATE 14, 14
PRINT "Valid Records =", Q

LOOP
```

Copyright © 1995 Sensible Technologies, Inc.          Emission Source Locator Software

```
'*****************calculate average data ************
FOR J = 1 TO 360
    IF ROSE1(J, 4) > 0 THEN XRose1(J) = ROSE1(J, 5) / ROSE1(J, 4)
    IF rose2(J, 4) > 0 THEN xROSE2(J) = rose2(J, 5) / rose2(J, 4)
    IF ROSE3(J, 4) > 0 THEN xROSE3(J) = ROSE3(J, 5) / ROSE3(J, 4)
    IF ROSE4(J, 4) > 0 THEN xROSE4(J) = ROSE4(J, 5) / ROSE4(J, 4)
    IF ROSE5(J, 4) > 0 THEN xROSE5(J) = ROSE5(J, 5) / ROSE5(J, 4)
    IF ROSE6(J, 4) > 0 THEN xROSE6(J) = ROSE6(J, 5) / ROSE6(J, 4)
    IF ROSE7(J, 4) > 0 THEN xROSE7(J) = ROSE7(J, 5) / ROSE7(J, 4)

Srose1(J) = XRose1(J)
    SROSE2(J) = xROSE2(J)
    SROSE3(J) = xROSE3(J)
    SROSE4(J) = xROSE4(J)
    SROSE5(J) = xROSE5(J)
    SROSE6(J) = xROSE6(J)
    SROSE7(J) = xROSE7(J)

NEXT J

CLOSE #1

END IF

IF ZIN2$ = "2" THEN '***SAVE DATA
    LOCATE 2, 1
    INPUT "Save Processed data as =", B$ OPEN B$ FOR OUTPUT AS #2
    PRINT #2, "ED data extract"
    FOR I = 1 TO 360
    PRINT #2, ROSE1(I, 1), ROSE1(I, 2), ROSE1(I, 3), ROSE1(I, 4), ROSE1(I, 5), XRose1(I), Srose1(I)
    PRINT #2, rose2(I, 1), rose2(I, 2), rose2(I, 3), rose2(I, 4), rose2(I, 5), xROSE2(I), SROSE2(I)
    PRINT #2, ROSE3(I, 1), ROSE3(I, 2), ROSE3(I, 3), ROSE3(I, 4), ROSE3(I, 5), xROSE3(I), SROSE3(I)
    PRINT #2, ROSE4(I, 1), ROSE4(I, 2), ROSE4(I, 3), ROSE4(I, 4), ROSE4(I, 5), xROSE4(I), SROSE4(I)
    PRINT #2, ROSE5(I, 1), ROSE5(I, 2), ROSE5(I, 3), ROSE5(I, 4), ROSE5(I, 5), xROSE5(I), SROSE5(I)
    PRINT #2, ROSE6(I, 1), ROSE6(I, 2), ROSE6(I, 3), ROSE6(I, 4), ROSE6(I, 5), xROSE6(I), SROSE6(I)
    PRINT #2, ROSE7(I, 1), ROSE7(I, 2), ROSE7(I, 3), ROSE7(I, 4), ROSE7(I, 5), xROSE7(I), SROSE7(I)
    NEXT I
    CLOSE #2

END IF

IF ZIN2$ = "3" THEN '*** GET PROCESSED DATA
    LOCATE 2, 1
    PRINT "                                          "
    LOCATE 2, 1
    INPUT "Input Processed data  =", B$
    FFFF$ = B$
    OPEN B$ FOR INPUT AS #2
    FOR JJ = 1 TO 360 'ZERO ARRAY
    FOR II = 1 TO 5
    ROSE1(JJ, II) = 0
    rose2(JJ, II) = 0
    ROSE3(JJ, II) = 0
    ROSE4(JJ, II) = 0
    ROSE5(JJ, II) = 0
    ROSE6(JJ, II) = 0
    ROSE7(JJ, II) = 0
    NEXT II
    NEXT JJ
```

Copyright © 1995 Sensible Technologies, Inc.                    Emission Source Locator Software

```
        INPUT #2, jjj$
        FOR I = 1 TO 360
        INPUT #2, ROSE1(I, 1), ROSE1(I, 2), ROSE1(I, 3), ROSE1(I, 4), ROSE1(I, 5), XRose1(I), Srose1(I)
        INPUT #2, rose2(I, 1), rose2(I, 2), rose2(I, 3). rose2(I, 4), rose2(I, 5), xROSE2(I), SROSE2(I)
        INPUT #2, ROSE3(I, 1), ROSE3(I, 2), ROSE3(I, 3), ROSE3(I, 4), ROSE3(I, 5), xROSE3(I), SROSE3(I)
        INPUT #2, ROSE4(I, 1), ROSE4(I, 2), ROSE4(I, 3), ROSE4(I, 4), ROSE4(I, 5), xROSE4(I), SROSE4(I)
        INPUT #2, ROSE5(I, 1), ROSE5(I, 2), ROSE5(I, 3), ROSE5(I, 4), ROSE5(I, 5), xROSE5(I), SROSE5(I)
        INPUT #2, ROSE6(I, 1), ROSE6(I, 2), ROSE6(I, 3), ROSE6(I, 4), ROSE6(I, 5), xROSE6(I), SROSE6(I)
        INPUT #2, ROSE7(I, 1), ROSE7(I, 2), ROSE7(I, 3), ROSE7(I, 4), ROSE7(I, 5), xROSE7(I), SROSE7(I)
        NEXT I
        CLOSE #2
    END IF
END IF IF ZIN$ = "3" THEN '***********DISPLAY*************
    LOCATE 2, 1
    PRINT "                                    "
    LOCATE 2, 1
    PRINT "1= WIND Rose FREQ. 2=MASS FLOW RoseS 3= CONC. calm 4= MAP "
    LOCATE 1, 8
    PRINT "   "
    LOCATE 1, 1
    ZIN3$ = ""
    INPUT "Option?", ZIN3S
        IF ZIN3$ = "1" THEN '***Wind Rose Frequency
        'find max value in wind Rose for scalling
        big = 0
        FOR I = 1 TO 360
        IF ROSE1(I, 2) > big THEN big = ROSE1(I, 2)
        NEXT I K = 2   'array element
        sc = 1
        IF big > 0 THEN sc = 220 / big'scale
        kolor = 9 'color lite blue
        CALL SHOWWIND(ROSE1(), 320, 240, K, sc, kolor)
    END IF IF ZIN3$ = "2" THEN '***Mass Flow Roses
    K = 7  ' element to plot
    kolor = 15'Bright White
    kolor = 0'RED
        '******plot Rose******
        CLS
        PAINT (1, 1), 15

CALL SHOW(Srose1(), xs(1), ys(1), K, SCALE, kolor)
        CALL SHOW(SROSE2(), xs(2), ys(2), K, SCALE, kolor)
        CALL SHOW(SROSE3(), xs(3), ys(3), K, SCALE, kolor)
        CALL SHOW(SROSE4(), xs(4), ys(4), K, SCALE, kolor)
        CALL SHOW(SROSE5(), xs(5), ys(5), K, SCALE, kolor)
        CALL SHOW(SROSE6(), xs(6), ys(6), K, SCALE, kolor)
        CALL SHOW(SROSE7(), xs(7), ys(7), K, SCALE, kolor)
        '*****************************TEMP
    'find max value in wind Rose for scalling
    big = 0
    FOR I = 1 TO 360
    IF ROSE1(I, 2) > big THEN big = ROSE1(I, 2)
    NEXT I K = 2   'array element
    sc = 1
    IF big > 0 THEN sc = 220 / big'scale
    kolor = 9 'color lite blue
    CALL SHOWWIND(ROSE1(), 320, 240, K, sc, kolor)
```

'*******************************END TEMP

Copyright © 1995 Sensible Technologies, Inc.  Emission Source Locator Software

```
            DO WHILE NOT INKEY$ = "B"
            LOOP

END IF
    IF ZIN3$ = "3" THEN '*** Conc. Roses
    '"vvvv"
            CLS
            PAINT (1, 1), 15
    K = 4   ' element to plot
    kolor = 1
        LOCATE 3, 1
        PRINT "Averages"
        LOCATE 3, 70
        PRINT "Number"
    FOR I = 1 TO 7 r! = rose2(I, 1) / rose2(I, 2)
    FOR fe = 1 TO 10
    LINE (xs(I) + fe, ys(I))-(xs(I) + fe, ys(I) - 2 * r!), kolor
    NEXT fe
        LOCATE 3 + I, 1
        PRINT USING "# = ##.##"; I; r!
        LOCATE 3 + I, 70
        PRINT rose2(I, 2)
    NEXT I

DO WHILE NOT INKEY$ = "B"
        LOOP

END IF
    IF ZIN3$ = "4" THEN '*** Map
      IF c1 = 0 THEN
      c1 = 6.5
      c2 = 6.2
      c3 = 5.4
      c4 = 5!
      END IF
      CALL SCRDP(xs(), ys(), c1, c2, c3, c4, c5)
    END IF
END IF

IF ZIN$ = "4" THEN '*************CLEAR***************
    CLS
    END IF

' "1=change settings 2=I/O 3=Display 4= Clear Screen"

LOOP
```

Copyright © 1995 Sensible Technologies, Inc.      25     Emission Source Locator Software

```
SUB ARCTAN (X%, Y%, DEG%)
X% = -X%
IF Y% = 0 THEN
  IF X% > 0 THEN
    DEG% = 90
    ELSE
    DEG% = 270
  END IF
ELSE
  IF X% = 0 THEN
    IF Y% > 0 THEN
    DEG% = 360
    ELSE
    DEG% = 180
    END IF
  ELSE
    X1% = ABS(X%)
    Y1% = ABS(Y%)
    IF Y1% > X1% THEN
      DEG1% = 90 - TABLE(FIX(58 * X1% / Y1%))
      'DEG1% = ATN(Y1% / X1%) * 180 / 3.1416
      IF Y% > 0 AND X% > 0 THEN
        DEG% = 90 - DEG1%
      ELSE
        IF Y% > 0 AND X% < 0 THEN
          DEG% = 270 + DEG1%
        ELSE
          IF Y% < 0 AND X% < 0 THEN
            DEG% = 270 - DEG1%
          ELSE
            DEG% = 90 + DEG1%
          END IF
        END IF
      END IF

ELSE
      DEG1% = TABLE(FIX(58 * Y1% / X1%))
      'DEG1% = ATN(Y1% / X1%) * 180 / 3.1416
      IF Y% > 0 AND X% > 0 THEN
        DEG% = 90 - DEG1%
      ELSE
        IF Y% > 0 AND X% < 0 THEN
          DEG% = 270 + DEG1%
        ELSE
          IF Y% < 0 AND X% < 0 THEN
            DEG% = 270 - DEG1%
          ELSE
            DEG% = 90 + DEG1%
          END IF
        END IF
      END IF

END IF
  END IF
END IF

IF DEG% = 0 THEN DEG% = 360

END SUB
```

Copyright © 1995 Sensible Technologies, Inc.    Emission Source Locator Software

```
DEFINT R
SUB CIT (XC(), YC(), Srose1(), SROSE2(), SROSE3(), SROSE4(), SROSE5(), SROSE6(), SROSE7(), cS1, cS2, cS3, cS4,
cS5)

DIM PEAK(1000)

FOR I = 1 TO 1000
     PEAK(I) = 0
   NEXT I
'FOR jout = 1 TO 50

' LOCATE 5, 10
  ' PRINT I, PEAK(25)

FOR IOUT = 1 TO 1000 STEP 1
     YL = INT(480 * RND + 1)
     XL = INT(640 * RND) + 1
     TAVG = 0
     H% = (YC(1) - YL)
     B% = (XC(1) - XL)
     CALL ARCTAN(B%, H%, Z%)
     TAVG = TAVG + Srose1(Z%)
     H% = (-YL + YC(2))
     B% = (XC(2) - XL)
     CALL ARCTAN(B%, H%, Z%)
     TAVG = TAVG + SROSE2(Z%)
     H% = (-YL + YC(3))
     B% = (XC(3) - XL)
     CALL ARCTAN(B%, H%, Z%)
     TAVG = TAVG + SROSE3(Z%)
     H% = (-YL + YC(4))
     B% = (XC(4) - XL)
     CALL ARCTAN(B%, H%, Z%)
     TAVG = TAVG + SROSE4(Z%)
     H% = (-YL + YC(5))
     B% = (XC(5) - XL)
     CALL ARCTAN(B%, H%, Z%)
     TAVG = TAVG + SROSE5(Z%)
     H% = (-YL + YC(6))
     B% = (XC(6) - XL)
     CALL ARCTAN(B%, H%, Z%)
     TAVG = TAVG + SROSE6(Z%)
     H% = (-YL + YC(7))
     B% = (XC(7) - XL)
     CALL ARCTAN(B%, H%, Z%)
     TAVG = TAVG + SROSE7(Z%)

'****AVERAGE DENSITY OF POINT SOURCE
    PEAK(IOUT) = TAVG / 7

NEXT IOUT
```

```
'*************SORT DATA

FOR I = 999 TO 1 STEP -1
LOCATE 5, 40
PRINT I, PEAK(1), PEAK(500)
  FOR J = 1 TO I
    IF PEAK(J) < PEAK(J + 1) THEN
      A = PEAK(J + 1)
      PEAK(J + 1) = PEAK(J)
      PEAK(J) = A
      'PRINT J, I, PEAK(J)
    END IF
  NEXT J
NEXT I
'*************END sORT

' NEXT jout
cS1 = PEAK(40)
cS2 = PEAK(80)
cS3 = PEAK(200)
cS4 = PEAK(400)
LOCATE 12, 1
PRINT PEAK(1), PEAK(50), PEAK(100), PEAK(200), PEAK(300)
END SUB DEFSNG R
'DEFINT R
'DEFDBL R '
SUB IRANDOM (RON())
'DEFINT R
FOR I = 1 TO 360
RON(I) = 0
RON(I) = 50 * RND(.0123)
g = RND(2)
IF g < .05 THEN I = I + 10

NEXT I

END SUB
```

```
'DEFINT S
SUB SCRDP (XxC(), YyC(), cD1, cD2, cD3, cD4, cD5)
CLS

'FOR XLS = 1 TO 8
FOR XLT = 320 TO 640

FOR XMOVE = 1 TO 2
  IF XMOVE = 2 THEN
  XL = XLT
  ELSE XL = 640 - XLT
  END IF
  IF NOT INKEY$ = "" THEN EXIT SUB
      FOR YL = 1 TO 480
   TAVG = 0
   H% = (-YL + YyC(1))
   B% = (XxC(1) - XL)
   CALL ARCTAN(B%. H%, Z%)
   TAVG = TAVG + Srose1(Z%)
   H% = (-YL + YyC(2))
   B% = (XxC(2) - XL)
   CALL ARCTAN(B%, H%, Z%)
   TAVG = TAVG + SROSE2(Z%)
   H% = (-YL + YyC(3))
   B% = (XxC(3) - XL)
   CALL ARCTAN(B%, H%, Z%)
   TAVG = TAVG + SROSE3(Z%)
   H% = (-YL + YyC(4))
   B% = (XxC(4) - XL)
   CALL ARCTAN(B%, H%, Z%)
   TAVG = TAVG + SROSE4(Z%)
   H% = (-YL + YyC(5))
   B% = (XxC(5) - XL)
   CALL ARCTAN(B%, H%, Z%)
   TAVG = TAVG + SROSE5(Z%)
   H% = (-YL + YyC(6))
   B% = (XxC(6) - XL)
   CALL ARCTAN(B%, H%, Z%)
   TAVG = TAVG + SROSE6(Z%)
   H% = (-YL + YyC(7))
   B% = (XxC(7) - XL)
   CALL ARCTAN(B%, H%, Z%)
   TAVG = TAVG + SROSE7(Z%)
```

Copyright © 1995 Sensible Technologies, Inc.    39    Emission Source Locator Software

```
'****AVERAGE DENSITY OF POINT SOURCE
THEAVG = TAVG / 7
'****SET COLOR SEPARATION********
IF THEAVG > cD1 THEN
 CLR = 4  'RED
ELSE
  IF THEAVG > cD2 THEN
    CLR = 1'BLUE
  ELSE
   IF THEAVG > cD3 THEN
   CLR = 14 'YELLOW
   ELSE
    IF THEAVG > cD4 THEN
     CLR = 7 'WHITE
    ELSE
     CLR = 15 'BRIGHT WHITE
     'CLR = 0   'black
    END IF
   END IF
  END IF
END IF
IF BIGGEST < THEAVG THEN
BIGGEST = THEAVG
BIGX = XL
BIGY = YL
END IF

PSET (XL, YL), CLR      'THEAVG * (8 / 50)

' LOCATE 1, 60

' PRINT THEAVG
  'NEXT II
 NEXT YL
NEXT XMOVE
NEXT XLT

'NEXT XLS
'*************DRAW IN OUTLINE
LINE (XxC(1), YyC(1))-(XxC(5), YyC(5)), 0
LINE (XxC(5), YyC(5))-(XxC(7), YyC(7)), 0
LINE (XxC(7), YyC(7))-(XxC(6), YyC(6)), 0
LINE (XxC(6), YyC(6))-(XxC(4), YyC(4)), 0
LINE (XxC(4), YyC(4))-(XxC(3), YyC(3)), 0
LINE (XxC(3), YyC(3))-(XxC(2), YyC(2)), 0
LINE (XxC(2), YyC(2))-(XxC(1), YyC(1)), 0

FOR I = 1 TO 10 'VERTICAL LINE FROM HIGH READING DOWN
     PSET (BIGX, BIGY), 0
     BIGY = BIGY - 1
NEXT I

DO WHILE INKEY$ = ""
LOOP

END SUB
```

```
SUB SHOW (SROSEX(), xa, yb, K, SCALE, kolor)

convert = (3.141593 / 180)

FOR I = 1 TO 360
    X = xa + SROSEX(I) * SIN(convert * I) * SCALE
    Y = yb - SROSEX(I) * COS(convert * I) * SCALE
    LINE (xa, yb)-(X, Y), kolor   ' Rose
  NEXT I

END SUB

'DEFINT R
SUB SHOWWIND (RoseX(), xa, yb, K, SCALE, kolor)

convert = (3.141593 / 180)

FOR I = 1 TO 360
    X = xa + RoseX(I, K) * SIN(convert * I) * SCALE
    Y = yb - RoseX(I, K) * COS(convert * I) * SCALE
    LINE (xa, yb)-(X, Y), kolor   ' Rose
  NEXT I

END SUB

DEFINT R
SUB SMOOTH (XRose1(), Srose1())
Srose1(1) = .25 * XRose1(360) + .5 * XRose1(1) + .25 * XRose1(2)
FOR I = 2 TO 359
Srose1(I) = .25 * XRose1(I - 1) + .5 * XRose1(I) + .25 * XRose1(I + 1)
NEXT I
Srose1(360) = .25 * XRose1(359) + .5 * XRose1(360) + .25 * XRose1(1)

END SUB
```

```
'Emission Source Locator Software
'Copyright (C) 1995 Sensible Technologies, Inc.
'You can convert an angle measurement from degrees to radians by
'multiplying the degrees by ã/180, where ã = 3.141593.

'DEFINT R
DECLARE SUB CIT (XC(), YC(), Srose1(), SROSE2(), SROSE3(), SROSE4(), SROSE5(), SROSE6(), SROSE7(), c1, c2, c3, c4, c5)
DECLARE SUB IRANDOM (RON())
DECLARE SUB SHOW (Srose1(), X1, x2, K, SCALE, kolor)
DECLARE SUB SMOOTH (XRoseZ(), SROSEZ())
DECLARE SUB ARCTAN (X1%, Y1%, DEG%)
DECLARE SUB SCRDP (XC(), YC(), c1, c2, c3, c4, c5)
DECLARE SUB RAWIN (ROSE1(), rose2(), ROSE3(), ROSE4(), ROSE5(), ROSE6(), ROSE7())
'DECLARE SUB indata (A!)
'DECLARE SUB massRose (K!, SCALE!, kolor!)
DECLARE SUB SHOWWIND (ROSE1(), xa, yb, K, SCALE, kolor)
CLEAR , , 40000

NELE% = 360
FIVE% = 5
SIXTY% = 60

DIM SHARED ROSE1(NELE%, FIVE%)
DIM SHARED XRose1(NELE%)
DIM SHARED Srose1(NELE%)
DIM SHARED rose2(NELE%, FIVE%)
DIM SHARED xROSE2(NELE%)
DIM SHARED SROSE2(NELE%)
DIM SHARED ROSE3(NELE%, FIVE%)
DIM SHARED xROSE3(NELE%)
DIM SHARED SROSE3(NELE%)
DIM SHARED ROSE4(NELE%, FIVE%)
DIM SHARED xROSE4(NELE%)
DIM SHARED SROSE4(NELE%)
DIM SHARED ROSE5(NELE%, FIVE%)
DIM SHARED xROSE5(NELE%)
DIM SHARED SROSE5(NELE%)
DIM SHARED ROSE6(NELE%, FIVE%)
DIM SHARED xROSE6(NELE%)
DIM SHARED SROSE6(NELE%)
DIM SHARED ROSE7(NELE%, FIVE%)
DIM SHARED xROSE7(NELE%)
DIM SHARED SROSE7(NELE%)
DIM SHARED TABLE(SIXTY%)

'Element 1 is total velocity #
'Element 2 is number of samples in velocity number
'Element 3 is total concentration #
'Element 4 is number of samples in concentration
'Element 5 is Total mass flow #
'Element 6 is average mass flow
'Element 7 is smoothed mass flow 'Main element corresponds in element number to direction
DIM XC(7), YC(7), xs(7), ys(7)
DIM lc$(7), lcx$(7), SCALE, FFFF$ '***********LOAD DATA TABLE
'SET UP TABLE OF ARCTAN VALUES FOR USE BY ARCTAN SUBROUTINE
'==========================================================
'CODE BETWEEN =========== MUST BE IN THE MAIN PROGRAM pi = 3.1416
```

CLS

```
'CALCULATE TABLE VALUES
FOR I = 0 TO 58
TABLE(I) = FIX((ATN(I / 58) * 180 / pi) + .5)
'  PRINT USING "###   ###.####"; i; TABLE(i)
NEXT I

'ron is used as temporary storage array

SCREEN 12
K = 7  ' element to plot
kolor = 15'Bright White
         c1 = 82 'defalt color cuts
         c2 = 75
         c3 = 50
         c4 = 25

SCALE = 6'*********scaling factor
'*******Defalt location of AQMS stations
YC(1) = 120
     XC(1) = 100
YC(2) = 120
     XC(2) = 204
YC(3) = 120
     XC(3) = 332
YC(4) = 120
     XC(4) = 409
YC(5) = 271
     XC(5) = 166
YC(6) = 260
     XC(6) = 424
YC(7) = 399
     XC(7) = 307
FOR I = 1 TO 7
     xs(I) = XC(I)
     ys(I) = YC(I)
NEXT I
convert = (3.141593 / 180) 'Constatnt
SMTH$ = "." ' LEVEL OF SMOOTHING 0=NONE
ZIN$ = ""
DO WHILE NOT ZIN$ = "Q"
LOCATE 2, 1 'CLEAR LINE 2
PRINT "                                               "
LOCATE 2, 1 'PRINT MENU ON LINE 2
PRINT "1= Change settings  2= I/O  3= Display  4= Clear Screen"
LOCATE 1, 8
PRINT "           "; FFFF$; " "; c1; c2; c3; c4; SM
LOCATE 1, 1 ' PROMPT FOR MAIN OPTIONS
INPUT "Option?", ZIN$ IF ZIN$ = "1" THEN '************CHANGE SETTINGS*************
     LOCATE 2, 1
     PRINT "                                               "
     LOCATE 2, 1
     PRINT "1= SMOOTING  2= ROSE SCALE 3= SCREEN COLOR CUTS 4= SCALE SITE"
     ZIN1$ = ""
     LOCATE 1, 8
     PRINT "  "
     LOCATE 1, 1
     INPUT "Option?", ZIN1$
```

```
IF ZIN1$ = "1" THEN '****SMOOTHING
'INSERT 1
'INSERT 1

' LOCATE 1, 1
' ZIN4$ = ""
' INPUT "Option?", ZIN4$
LOCATE 2, 1' CLEAR INSTRUCTION LINE
PRINT "                              "
LOCATE 2, 1
PRINT "0= NO SMOOTHING  #=LEVEL OF SMOOTING"
SMTH$ = "."
LOCATE 1, 8
PRINT "   "
LOCATE 1, 1
INPUT "Option?", SMTH$
SM = VAL(SMTH$)
  IF SM = 0 THEN
      FOR J = 1 TO 360

Srose1(J) = XRose1(J)
            SROSE2(J) = xROSE2(J)
            SROSE3(J) = xROSE3(J)
            SROSE4(J) = xROSE4(J)
            SROSE5(J) = xROSE5(J)
            SROSE6(J) = xROSE6(J)
            SROSE7(J) = xROSE7(J)
      NEXT J
  END IF
  IF SM > 0 THEN
      FOR I = 1 TO SM
            CALL SMOOTH(Srose1(), Srose1())
            CALL SMOOTH(SROSE2(), SROSE2())
            CALL SMOOTH(SROSE3(), SROSE3())
            CALL SMOOTH(SROSE4(), SROSE4())
            CALL SMOOTH(SROSE5(), SROSE5())
            CALL SMOOTH(SROSE6(), SROSE6())
            CALL SMOOTH(SROSE7(), SROSE7())

NEXT I
  END IF

END IF

IF ZIN1$ = "2" THEN '***SCALE ROSE

' LOCATE 1, 1
' ZIN5$ = ""
' INPUT "Option?", ZIN5$
LOCATE 2, 1' CLEAR INSTRUCTION LINE
PRINT "                              "
LOCATE 2, 1
PRINT "INPUT SCALE FACTOR 1.0 = NO CHANGE"
LOCATE 1, 8
PRINT "   "
LOCATE 1, 1
HX = 1!
INPUT "Option?", HX
IF HX > 0 THEN
SCALE = SCALE * HX
END IF
END IF
```

```
IF ZIN1$ = "3" THEN '*** COLOR CUTS
   LOCATE 2, 1' CLEAR INSTRUCTION LINE
   PRINT "                                    "
   LOCATE 2, 1
   PRINT "c1+=red c2+=blue c3+=yellow c4+=gray >c4=white"
   SMTH$ = "."

LOCATE 2, 50
   INPUT "New C's", c1, c2, c3, c4

END IF

IF ZIN1$ = "5" THEN '*** SCALE SITE
   CALL CIT(xs(), ys(), Srose1(), SROSE2(), SROSE3(), SROSE4(), SROSE5(), SROSE6(), SROSE7(), c1,
c2, c3, c4, c5)

END IF

IF ZIN1$ = "4" THEN '*** SCALE SITE
   LOCATE 1, 1
   PRINT "           "
   LOCATE 2, 1' CLEAR INSTRUCTION LINE
   PRINT "                              "
   LOCATE 2, 1
   PRINT "PO1 X="; xs(1); " Y="; ys(1);
   LOCATE 2, 25
   INPUT "INPUT NEW X,Y", XN!, YN!
   PRINT "                              "
   LOCATE 2, 1
   INPUT "INPUT SCALLING FACTOR", SIZING!

A = XN!
   B = xs(1)

DXP = A - B
   A = YN!
   B = ys(1)

DYP = A - B
   FOR I = 1 TO 7
   xs(I) = XC(I) + DXP
   ys(I) = YC(I) + DYP
      BIC = (xs(I) - xs(1)) * SIZING
      'BIC = BIC * SIZING
   xs(I) = xs(1) + BIC
   'PRINT SIZING!; XS(1), XS(I); XC(I)
      BIC = (ys(I) - ys(1)) * SIZING
      'BIC = BIC * SIZING
   ys(I) = ys(1) + BIC
   'PRINT SIZING!; XS(1), XS(I); XC(I); BIC
   NEXT I

END IF
END IF
```

```
IF ZIN$ = "2" THEN '*************I/O***************
    LOCATE 2, 1
    PRINT "                                             "
    LOCATE 2, 1
    PRINT "1= Process Raw Data File  2= Save Processed Data 3= Get Process Data"
    ZIN2$ = ""
    LOCATE 1, 8
    PRINT "  "
    LOCATE 1, 1
    INPUT "Option?", ZIN2$ IF ZIN2$ = "1" THEN '***PROCESS RAW DATA
' OPEN file [FOR mode] [ACCESS access] [lock] AS [#]filenum [LEN=reclen]
            LOCATE 2, 1
            PRINT "                                         "
            LOCATE 2, 1
            INPUT "Raw Data File Name =", B$
            FFFF$ = B$
            OPEN B$ FOR INPUT AS #1
            LOCATE 3, 1
            FOR I = 1 TO 13
            INPUT #1, A$
            PRINT A$;
            NEXT I
            PRINT ""

'Element 1 is total velocity #
            'Element 2 is number of samples in velocity number
            'Element 3 is total concentration #
            'Element 4 is number of samples in concentration
            'Element 5 is Total mass flow #
            'xrose is average mass flow
            'srose is smoothed mass flow
                '***************get raw data for non calm data***************
            'Rose 2 elements 1 and 2 contain calm concentrations and frequency

Q = 0
            DO WHILE NOT EOF(1)

INPUT #1, Idate$, ItimeS, IWspeed$, IWspeedx$, Idir$, Idirx$, Isec$, Isecx$, Id$, Ic$(1), Icx$(1), Ic$(2),
Icx$(2), Ic$(3), Icx$(3), Ic$(4), Icx$(4), Ic$(5), IcxS(5), Ic$(6), Icx$(6), Ic$(7), Icx$(7)
                IWspeed = VAL(IWspeed$)

IF IWspeedx$ = "v" AND IWspeed < 1.01 THEN 'capture calm cond
                  FOR I = 1 TO 7
                  IF Icx$(I) = "v" THEN
                    rose2(I, 1) = VAL(Ic$(I)) + rose2(I, 1)
                    rose2(I, 2) = rose2(I, 2) + 1
                  END IF
                  NEXT I
                END IF IF IWspeedx$ = "v" AND IWspeed > 1 THEN 'valid wind speed
                    Q = Q + 1
                    D = VAL(Idir$)'direction in degrees

D = D + 44
```

```
'**********adjust angle
    IF D > 360 THEN D = D - 360

ROSE1(D, 1) = ROSE1(D, 1) + IWspeed
    ROSE1(D, 2) = ROSE1(D, 2) + 1
 IF IcxS(1) = "v" THEN
    conc = VAL(Ic$(1))
    ROSE1(D, 3) = ROSE1(D, 3) + conc'set concentration into array
    ROSE1(D, 4) = ROSE1(D, 4) + 1
    ROSE1(D, 5) = ROSE1(D, 5) + IWspeed * conc
    IF ROSE1(D, 5) > 32000 THEN PRINT "tilt1"

END IF
IF Icx$(2) = "v" THEN
    conc = VAL(Ic$(2))
    rose2(D, 3) = rose2(D, 3) + conc'set concentration into array
    rose2(D, 4) = rose2(D, 4) + 1
    rose2(D, 5) = rose2(D, 5) + IWspeed * conc
    IF rose2(D, 5) > 32000 THEN PRINT "tilt2"
END IF
IF IcxS(3) = "v" THEN
    conc = VAL(Ic$(3))
    ROSE3(D, 3) = ROSE3(D, 3) + conc'set concentration into array
    ROSE3(D, 4) = ROSE3(D, 4) + 1
    ROSE3(D, 5) = ROSE3(D, 5) + IWspeed * conc
    IF ROSE3(D, 5) > 32000 THEN PRINT "tilt3"
END IF
IF Icx$(4) = "v" THEN
    conc = VAL(Ic$(4))
    ROSE4(D, 3) = ROSE4(D, 3) + conc'set concentration into array
    ROSE4(D, 4) = ROSE4(D, 4) + 1
    ROSE4(D, 5) = ROSE4(D, 5) + IWspeed * conc
    IF ROSE4(D, 5) > 32000 THEN PRINT "tilt4"
END IF
IF IcxS(5) = "v" THEN
    conc = VAL(Ic$(5))
    ROSE5(D, 3) = ROSE5(D, 3) + conc'set concentration into array
    ROSE5(D, 4) = ROSE5(D, 4) + 1
    ROSE5(D, 5) = ROSE5(D, 5) + IWspeed * conc
    IF ROSE5(D, 5) > 32000 THEN PRINT "tilt5"
END IF
IF Icx$(6) = "v" THEN
    conc = VAL(Ic$(6))
    ROSE6(D, 3) = ROSE6(D, 3) + conc'set concentration into array
    ROSE6(D, 4) = ROSE6(D, 4) + 1
    ROSE6(D, 5) = ROSE6(D, 5) + IWspeed * conc
    IF ROSE6(D, 5) > 32000 THEN PRINT "tilt6"
END IF
IF IcxS(7) = "v" THEN
    conc = VAL(Ic$(7))
    ROSE7(D, 3) = ROSE7(D, 3) + conc'set concentration into array
    ROSE7(D, 4) = ROSE7(D, 4) + 1
    ROSE7(D, 5) = ROSE7(D, 5) + IWspeed * conc
    IF ROSE7(D, 5) > 32000 THEN PRINT "tilt7"
    END IF
END IF LOCATE 14, 14
PRINT "Valid Records =", Q

LOOP
```

```
'****************calculate average data ************
FOR J = 1 TO 360
    IF ROSE1(J, 4) > 0 THEN XRose1(J) = ROSE1(J, 5) / ROSE1(J, 4)
    IF rose2(J, 4) > 0 THEN xROSE2(J) = rose2(J, 5) / rose2(J, 4)
    IF ROSE3(J, 4) > 0 THEN xROSE3(J) = ROSE3(J, 5) / ROSE3(J, 4)
    IF ROSE4(J, 4) > 0 THEN xROSE4(J) = ROSE4(J, 5) / ROSE4(J, 4)
    IF ROSE5(J, 4) > 0 THEN xROSE5(J) = ROSE5(J, 5) / ROSE5(J, 4)
    IF ROSE6(J, 4) > 0 THEN xROSE6(J) = ROSE6(J, 5) / ROSE6(J, 4)
    IF ROSE7(J, 4) > 0 THEN xROSE7(J) = ROSE7(J, 5) / ROSE7(J, 4)

Srose1(J) = XRose1(J)
    SROSE2(J) = xROSE2(J)
    SROSE3(J) = xROSE3(J)
    SROSE4(J) = xROSE4(J)
    SROSE5(J) = xROSE5(J)
    SROSE6(J) = xROSE6(J)
    SROSE7(J) = xROSE7(J)

NEXT J

CLOSE #1

END IF

IF ZIN2$ = "2" THEN '***SAVE DATA
    LOCATE 2, 1
    INPUT "Save Processed data as =", B$ OPEN B$ FOR OUTPUT AS #2
    PRINT #2, "ED data extract"
    FOR I = 1 TO 360
    PRINT #2, ROSE1(I, 1), ROSE1(I, 2), ROSE1(I, 3), ROSE1(I, 4), ROSE1(I, 5), XRose1(I), Srose1(I)
    PRINT #2, rose2(I, 1), rose2(I, 2), rose2(I, 3), rose2(I, 4), rose2(I, 5), xROSE2(I), SROSE2(I)
    PRINT #2, ROSE3(I, 1), ROSE3(I, 2), ROSE3(I, 3), ROSE3(I, 4), ROSE3(I, 5), xROSE3(I), SROSE3(I)
    PRINT #2, ROSE4(I, 1), ROSE4(I, 2), ROSE4(I, 3), ROSE4(I, 4), ROSE4(I, 5), xROSE4(I), SROSE4(I)
    PRINT #2, ROSE5(I, 1), ROSE5(I, 2), ROSE5(I, 3), ROSE5(I, 4), ROSE5(I, 5), xROSE5(I), SROSE5(I)
    PRINT #2, ROSE6(I, 1), ROSE6(I, 2), ROSE6(I, 3), ROSE6(I, 4), ROSE6(I, 5), xROSE6(I), SROSE6(I)
    PRINT #2, ROSE7(I, 1), ROSE7(I, 2), ROSE7(I, 3), ROSE7(I, 4), ROSE7(I, 5), xROSE7(I), SROSE7(I)
    NEXT I
    CLOSE #2

END IF

IF ZIN2$ = "3" THEN '*** GET PROCESSED DATA
    LOCATE 2, 1
    PRINT "                                      "
    LOCATE 2, 1
    INPUT "Input Processed data  =", B$
    FFFF$ = B$
    OPEN B$ FOR INPUT AS #2
    FOR JJ = 1 TO 360 'ZERO ARRAY
        FOR II = 1 TO 5
            ROSE1(JJ, II) = 0
            rose2(JJ, II) = 0
            ROSE3(JJ, II) = 0
            ROSE4(JJ, II) = 0
            ROSE5(JJ, II) = 0
            ROSE6(JJ, II) = 0
            ROSE7(JJ, II) = 0
        NEXT II
    NEXT JJ
```

```
        INPUT #2, jjj$
        FOR I = 1 TO 360
        INPUT #2, ROSE1(I, 1), ROSE1(I, 2), ROSE1(I, 3), ROSE1(I, 4), ROSE1(I, 5), XRose1(I), Srose1(I)
        INPUT #2, rose2(I, 1), rose2(I, 2), rose2(I, 3), rose2(I, 4), rose2(I, 5), xROSE2(I), SROSE2(I)
        INPUT #2, ROSE3(I, 1), ROSE3(I, 2), ROSE3(I, 3), ROSE3(I, 4), ROSE3(I, 5), xROSE3(I), SROSE3(I)
        INPUT #2, ROSE4(I, 1), ROSE4(I, 2), ROSE4(I, 3), ROSE4(I, 4), ROSE4(I, 5), xROSE4(I), SROSE4(I)
        INPUT #2, ROSE5(I, 1), ROSE5(I, 2), ROSE5(I, 3), ROSE5(I, 4), ROSE5(I, 5), xROSE5(I), SROSE5(I)
        INPUT #2, ROSE6(I, 1), ROSE6(I, 2), ROSE6(I, 3), ROSE6(I, 4), ROSE6(I, 5), xROSE6(I), SROSE6(I)
        INPUT #2, ROSE7(I, 1), ROSE7(I, 2), ROSE7(I, 3), ROSE7(I, 4), ROSE7(I, 5), xROSE7(I), SROSE7(I)
        NEXT I
        CLOSE #2
    END IF
END IF IF ZIN$ = "3" THEN '***********DISPLAY*************
    LOCATE 2, 1
    PRINT "                                              "
    LOCATE 2, 1
    PRINT "1= WIND Rose FREQ.  2=MASS FLOW  RoseS  3= CONC. calm 4= MAP "
    LOCATE 1, 8
    PRINT "   "
    LOCATE 1, 1
    ZIN3$ = ""
    INPUT "Option?", ZIN3$
        IF ZIN3$ = "1" THEN '***Wind Rose Frequency
        'find max value in wind Rose for scalling
        big = 0
        FOR I = 1 TO 360
        IF ROSE1(I, 2) > big THEN big = ROSE1(I, 2)
        NEXT I K = 2   'array element
        sc = 1
        IF big > 0 THEN sc = 220 / big'scale
        kolor = 9 'color lite blue
        CALL SHOWWIND(ROSE1(), 320, 240, K, sc, kolor)
    END IF IF ZIN3$ = "2" THEN '***Mass Flow Roses
    K = 7   ' element to plot
    kolor = 15'Bright White
    kolor = 0'RED
        '******plot Rose******
        CLS
        PAINT (1, 1), 15

CALL SHOW(Srose1(), xs(1), ys(1), K, SCALE, kolor)
        CALL SHOW(SROSE2(), xs(2), ys(2), K, SCALE, kolor)
        CALL SHOW(SROSE3(), xs(3), ys(3), K, SCALE, kolor)
        CALL SHOW(SROSE4(), xs(4), ys(4), K, SCALE, kolor)
        CALL SHOW(SROSE5(), xs(5), ys(5), K, SCALE, kolor)
        CALL SHOW(SROSE6(), xs(6), ys(6), K, SCALE, kolor)
        CALL SHOW(SROSE7(), xs(7), ys(7), K, SCALE, kolor)
        '***************************TEMP
    'find max value in wind Rose for scalling
    big = 0
    FOR I = 1 TO 360
    IF ROSE1(I, 2) > big THEN big = ROSE1(I, 2)
    NEXT I K = 2   'array element
    sc = 1
    IF big > 0 THEN sc = 220 / big'scale
    kolor = 9 'color lite blue
    CALL SHOWWIND(ROSE1(), 320, 240, K, sc, kolor)
```

`'*****************************END TEMP`

```
            DO WHILE NOT INKEY$ = "B"
            LOOP

END IF
    IF ZIN3$ = "3" THEN '*** Conc. Roses
    "'vvvv"
            CLS
            PAINT (1, 1), 15
    K = 4  ' element to plot
    kolor = 1
            LOCATE 3, 1
            PRINT "Averages"
            LOCATE 3, 70
            PRINT "Number"
    FOR I = 1 TO 7 r! = rose2(I, 1) / rose2(I, 2)
      FOR fe = 1 TO 10
      LINE (xs(I) + fe, ys(I))-(xs(I) + fe, ys(I) - 2 * r!), kolor
      NEXT fe
            LOCATE 3 + I, 1
            PRINT USING "# = ##.##": I; r!
            LOCATE 3 + I, 70
            PRINT rose2(I, 2)
    NEXT I

DO WHILE NOT INKEY$ = "B"
            LOOP

END IF
    IF ZIN3$ = "4" THEN '*** Map
      IF c1 = 0 THEN
      c1 = 6.5
      c2 = 6.2
      c3 = 5.4
      c4 = 5!
      END IF
      CALL SCRDP(xs(), ys(), c1, c2, c3, c4, c5)
    END IF
END IF

IF ZIN$ = "4" THEN '************CLEAR***************
    CLS
    END IF

' "1=change settings 2=I/O 3=Display 4= Clear Screen"

LOOP
```

```
SUB ARCTAN (X%, Y%, DEG%)
X% = -X%
IF Y% = 0 THEN
  IF X% > 0 THEN
    DEG% = 90
    ELSE
    DEG% = 270
  END IF
ELSE
  IF X% = 0 THEN
    IF Y% > 0 THEN
    DEG% = 360
    ELSE
    DEG% = 180
    END IF
  ELSE
    X1% = ABS(X%)
    Y1% = ABS(Y%)
    IF Y1% > X1% THEN
      DEG1% = 90 - TABLE(FIX(58 * X1% / Y1%))
      'DEG1% = ATN(Y1% / X1%) * 180 / 3.1416
      IF Y% > 0 AND X% > 0 THEN
        DEG% = 90 - DEG1%
      ELSE
        IF Y% > 0 AND X% < 0 THEN
          DEG% = 270 + DEG1%
        ELSE
          IF Y% < 0 AND X% < 0 THEN
            DEG% = 270 - DEG1%
          ELSE
            DEG% = 90 + DEG1%
          END IF
        END IF
      END IF

ELSE
      DEG1% = TABLE(FIX(58 * Y1% / X1%))
      'DEG1% = ATN(Y1% / X1%) * 180 / 3.1416
      IF Y% > 0 AND X% > 0 THEN
        DEG% = 90 - DEG1%
      ELSE
        IF Y% > 0 AND X% < 0 THEN
          DEG% = 270 + DEG1%
        ELSE
          IF Y% < 0 AND X% < 0 THEN
            DEG% = 270 - DEG1%
          ELSE
            DEG% = 90 + DEG1%
          END IF
        END IF
      END IF

END IF
  END IF
END IF

IF DEG% = 0 THEN DEG% = 360

END SUB
```

```
DEFINT R
SUB CIT (XC(), YC(), Srose1(), SROSE2(), SROSE3(), SROSE4(), SROSE5(), SROSE6(), SROSE7(), cS1, cS2, cS3, cS4,
cS5)

DIM PEAK(1000)

FOR I = 1 TO 1000
    PEAK(I) = 0
  NEXT I
'FOR jout = 1 TO 50

' LOCATE 5, 10
 ' PRINT I, PEAK(25)

FOR IOUT = 1 TO 1000 STEP 1
    YL = INT(480 * RND + 1)
    XL = INT(640 * RND) + 1
    TAVG = 0
    H% = (YC(1) - YL)
    B% = (XC(1) - XL)
    CALL ARCTAN(B%, H%, Z%)
    TAVG = TAVG + Srose1(Z%)
    H% = (-YL + YC(2))
    B% = (XC(2) - XL)
    CALL ARCTAN(B%, H%, Z%)
    TAVG = TAVG + SROSE2(Z%)
    H% = (-YL + YC(3))
    B% = (XC(3) - XL)
    CALL ARCTAN(B%, H%, Z%)
    TAVG = TAVG + SROSE3(Z%)
    H% = (-YL + YC(4))
    B% = (XC(4) - XL)
    CALL ARCTAN(B%, H%, Z%)
    TAVG = TAVG + SROSE4(Z%)
    H% = (-YL + YC(5))
    B% = (XC(5) - XL)
    CALL ARCTAN(B%, H%, Z%)
    TAVG = TAVG + SROSE5(Z%)
    H% = (-YL + YC(6))
    B% = (XC(6) - XL)
    CALL ARCTAN(B%, H%, Z%)
    TAVG = TAVG + SROSE6(Z%)
    H% = (-YL + YC(7))
    B% = (XC(7) - XL)
    CALL ARCTAN(B%, H%, Z%)
    TAVG = TAVG + SROSE7(Z%)

'****AVERAGE DENSITY OF POINT SOURCE
    PEAK(IOUT) = TAVG / 7

NEXT IOUT
```

Copyright © 1995 Sensible Technologies, Inc.     Emission Source Locator Software

```
'**************SORT DATA

FOR I = 999 TO 1 STEP -1
LOCATE 5, 40
PRINT I, PEAK(1), PEAK(500)
  FOR J = 1 TO I
    IF PEAK(J) < PEAK(J + 1) THEN
      A = PEAK(J + 1)
      PEAK(J + 1) = PEAK(J)
      PEAK(J) = A
     'PRINT J, I, PEAK(J)
    END IF
  NEXT J
NEXT I
'*************END sORT

' NEXT jout
cS1 = PEAK(40)
cS2 = PEAK(80)
cS3 = PEAK(200)
cS4 = PEAK(400)
LOCATE 12, 1
PRINT PEAK(1), PEAK(50), PEAK(100), PEAK(200), PEAK(300)
END SUB DEFSNG R
'DEFINT R
'DEFDBL R '
SUB IRANDOM (RON())
'DEFINT R
FOR I = 1 TO 360
RON(I) = 0
RON(I) = 50 * RND(.0123)
g = RND(2)
IF g < .05 THEN I = I + 10

NEXT I

END SUB
```

Copyright © 1995 Sensible Technologies, Inc.    45    Emission Source Locator Software

```
'DEFINT S
SUB SCRDP (XxC(), YyC(), cD1, cD2, cD3, cD4, cD5)
CLS

'FOR XLS = 1 TO 8
FOR XLT = 320 TO 640

FOR XMOVE = 1 TO 2
   IF XMOVE = 2 THEN
   XL = XLT
   ELSE XL = 640 - XLT
   END IF
   IF NOT INKEY$ = "" THEN EXIT SUB
       FOR YL = 1 TO 480
    TAVG = 0
    H% = (-YL + YyC(1))
    B% = (XxC(1) - XL)
    CALL ARCTAN(B%, H%, Z%)
    TAVG = TAVG + Srose1(Z%)
    H% = (-YL + YyC(2))
    B% = (XxC(2) - XL)
    CALL ARCTAN(B%, H%, Z%)
    TAVG = TAVG + SROSE2(Z%)
    H% = (-YL + YyC(3))
    B% = (XxC(3) - XL)
    CALL ARCTAN(B%, H%, Z%)
    TAVG = TAVG + SROSE3(Z%)
    H% = (-YL + YyC(4))
    B% = (XxC(4) - XL)
    CALL ARCTAN(B%, H%, Z%)
    TAVG = TAVG + SROSE4(Z%)
    H% = (-YL + YyC(5))
    B% = (XxC(5) - XL)
    CALL ARCTAN(B%, H%, Z%)
    TAVG = TAVG + SROSE5(Z%)
    H% = (-YL + YyC(6))
    B% = (XxC(6) - XL)
    CALL ARCTAN(B%, H%, Z%)
    TAVG = TAVG + SROSE6(Z%)
    H% = (-YL + YyC(7))
    B% = (XxC(7) - XL)
    CALL ARCTAN(B%, H%, Z%)
    TAVG = TAVG + SROSE7(Z%)
```

Copyright © 1995 Sensible Technologies, Inc.  Emission Source Locator Software

```
'****AVERAGE DENSITY OF POINT SOURCE
THEAVG = TAVG / 7
'****SET COLOR SEPARATION********
IF THEAVG > cD1 THEN
  CLR = 4 'RED
ELSE
  IF THEAVG > cD2 THEN
    CLR = 1 'BLUE
  ELSE
    IF THEAVG > cD3 THEN
      CLR = 14 'YELLOW
    ELSE
      IF THEAVG > cD4 THEN
        CLR = 7 'WHITE
      ELSE
        CLR = 15 'BRIGHT WHITE
        'CLR = 0  'black
      END IF
    END IF
  END IF
END IF
IF BIGGEST < THEAVG THEN
BIGGEST = THEAVG
BIGX = XL
BIGY = YL
END IF

PSET (XL, YL), CLR    'THEAVG * (8 / 50)

' LOCATE 1, 60

' PRINT THEAVG
 'NEXT II
 NEXT YL
NEXT XMOVE
NEXT XLT

'NEXT XLS
'************DRAW IN OUTLINE
LINE (XxC(1), YyC(1))-(XxC(5), YyC(5)), 0
LINE (XxC(5), YyC(5))-(XxC(7), YyC(7)), 0
LINE (XxC(7), YyC(7))-(XxC(6), YyC(6)), 0
LINE (XxC(6), YyC(6))-(XxC(4), YyC(4)), 0
LINE (XxC(4), YyC(4))-(XxC(3), YyC(3)), 0
LINE (XxC(3), YyC(3))-(XxC(2), YyC(2)), 0
LINE (XxC(2), YyC(2))-(XxC(1), YyC(1)), 0

FOR I = 1 TO 10 'VERTICAL LINE FROM HIGH READING DOWN
    PSET (BIGX, BIGY), 0
    BIGY = BIGY - 1
NEXT I

DO WHILE INKEYS = ""
LOOP

END SUB
```

Copyright © 1995 Sensible Technologies, Inc.        Emission Source Locator Software

```
SUB SHOW (SROSEX(), xa, yb, K, SCALE, kolor)

convert = (3.141593 / 180)

FOR I = 1 TO 360
   X = xa + SROSEX(I) * SIN(convert * I) * SCALE
   Y = yb - SROSEX(I) * COS(convert * I) * SCALE
   LINE (xa, yb)-(X, Y), kolor   ' Rose
 NEXT I

END SUB

'DEFINT R
SUB SHOWWIND (RoseX(), xa, yb, K, SCALE, kolor)

convert = (3.141593 / 180)

FOR I = 1 TO 360
   X = xa + RoseX(I, K) * SIN(convert * I) * SCALE
   Y = yb - RoseX(I, K) * COS(convert * I) * SCALE
   LINE (xa, yb)-(X, Y), kolor   ' Rose
 NEXT I

END SUB

DEFINT R
SUB SMOOTH (XRose1(), Srose1())
Srose1(1) = .25 * XRose1(360) + .5 * XRose1(1) + .25 * XRose1(2)
FOR I = 2 TO 359
Srose1(I) = .25 * XRose1(I - 1) + .5 * XRose1(I) + .25 * XRose1(I + 1)
NEXT I
Srose1(360) = .25 * XRose1(359) + .5 * XRose1(360) + .25 * XRose1(1)

END SUB
```

I claim:

1. A method of mapping the location of one or more sources of material emitted into a moving fluid comprising the steps of:

measuring reasonably simultaneously the concentration of the emitted material, the direction of movement of the fluid and the velocity of the fluid at a plurality of sensing points over a period of time;

calculating the directional mass flux of the material in each direction of fluid flux at each sensing point over the period of time;

calculating the relative emission value of emitted material at each point in a plane around the sensing points by summing contributions at each said point in said plain of the plurality of determined directional mass fluxes.

2. A method as in claim one including smoothing the mass flux value for each direction by including a contribution from each of the adjacent mass flux values.

3. A method as in claim 2 wherein the smoothed mass flux is calculated by adding 25% of each of the adjacent mass fluxes to 50% of the directional mass flux for each wind direction angle.

4. A method as in claim two wherein the measurements of concentration, direction and velocity are discarded for low velocity values.

5. A method as in claim 2 wherein the measurements of concentration, direction and velocity are discarded from the sensing point nearest to a source of emitted materials.

6. A method as in claim one wherein the measurements of concentration, direction and velocity are discarded for low velocity values.

7. A method as in claims 1 wherein the measurements of concentration, direction and velocity are discarded from the sensing point nearest to a source of emitted materials.

* * * * *